United States Patent [19]

Spingler

[11] Patent Number: 5,108,392
[45] Date of Patent: Apr. 28, 1992

[54] COAGULATION FORCEPS AND METHOD OF FABRICATING THE SAME

[75] Inventor: Rolf A. Spingler, Lottstetten-Nack, Fed. Rep. of Germany

[73] Assignee: United States Surgical Corporation, Norwalk, Conn.

[21] Appl. No.: 746,141

[22] Filed: Aug. 14, 1991

Related U.S. Application Data

[63] Continuation of Ser. No. 518,496, May 3, 1990, abandoned, which is a continuation of Ser. No. 207,399, Jun. 16, 1988, abandoned.

[30] Foreign Application Priority Data

Jun. 17, 1987 [DE] Fed. Rep. of Germany ....... 3720215
Jul. 4, 1987 [DE] Fed. Rep. of Germany ....... 3722142

[51] Int. Cl.⁵ .................... A61B 17/30; A61B 17/36
[52] U.S. Cl. .................... 606/51; 606/210; 294/99.2; 76/119
[58] Field of Search ........... 606/210, 211, 51, 52, 606/131; 294/99.2; 433/162, 157; 76/119, 101.1, DIG. 6

[56] References Cited

U.S. PATENT DOCUMENTS

| | | | |
|---|---|---|---|
| 966,325 | 8/1910 | Gilbert | 294/99.2 X |
| 985,755 | 2/1911 | Gilbert | 294/99.2 |
| 2,665,692 | 1/1954 | L'Esperance | 294/99.2 X |
| 3,653,388 | 4/1972 | Tenckhoff | |
| 3,653,389 | 4/1972 | Shannon | 606/210 |
| 4,074,718 | 2/1978 | Morrison | 606/51 X |
| 4,212,305 | 7/1980 | Lahay | 606/210 |
| 4,452,106 | 6/1984 | Tartagua | 606/210 X |
| 4,634,165 | 1/1987 | Russell et al. | |
| 4,793,349 | 12/1988 | Weinrib | |
| 4,938,214 | 7/1990 | Specht et al. | |

FOREIGN PATENT DOCUMENTS

| | | | |
|---|---|---|---|
| 92170 | 10/1983 | European Pat. Off. | 128/354 |
| 0133393 | 2/1985 | European Pat. Off. | |
| 0159453 | 10/1985 | European Pat. Off. | |
| 2577176 | 2/1977 | Fed. Rep. of Germany | |
| 3110666 | 8/1984 | Fed. Rep. of Germany | |
| 3430058 | 11/1987 | Fed. Rep. of Germany | |
| 2573301 | 5/1986 | France | |
| 1153898 | 5/1985 | U.S.S.R. | 606/210 |
| 2154930 | 9/1985 | United Kingdom | |

Primary Examiner—Michael H. Thaler
Attorney, Agent, or Firm—Thomas R. Bremer; Peter G. Dilworth; Rocco S. Barrese

[57] ABSTRACT

Tweezers or forceps, in particular coagulation forceps, comprising two forcep arms which each have a free gripping end and which delimit a slit-like space, preferably tapering from the gripping ends in the rest position, and which can be moved resiliently towards each other and which extend from a common closed zone, and a gripping element, is to be produced in a simple and inexpensive manner and is to provide a variety of uses. For that purpose the forceps comprise at least two shaped parts which subdivide the closed zone in the longitudinal direction and which are connected together with their inside surfaces bearing against each other. In addition the forceps are to be divided on their longitudinal axis and each of the shaped parts which are preferably of the same configuration comprise one half of both forcep arms.

20 Claims, 2 Drawing Sheets

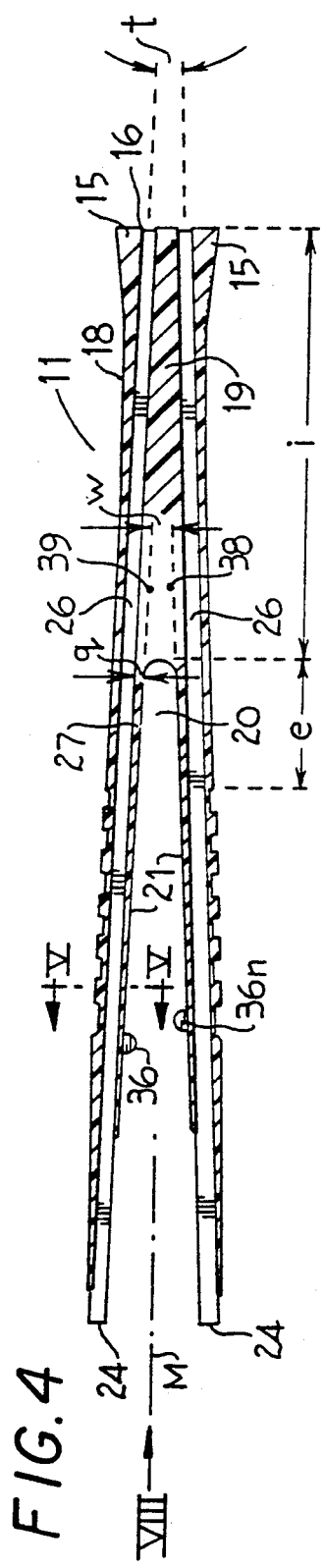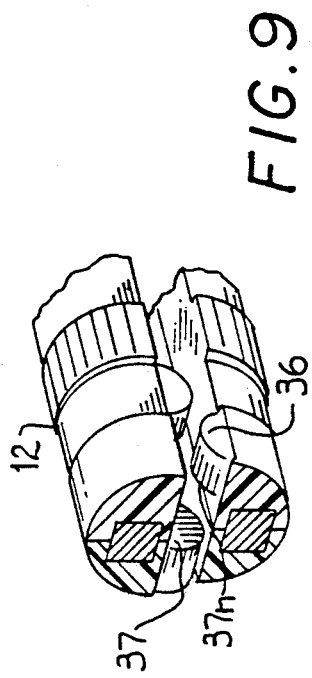

COAGULATION FORCEPS AND METHOD OF FABRICATING THE SAME

This is a continuation of copending application Ser. No. 07/518,496 filed on May 3, 1990, now abandoned, which was a continuation of U.S. application Ser. No. 07/207,399 filed Jun. 16, 1988, now abandoned.

BACKGROUND OF THE INVENTION

The present invention relates to tweezers or forceps, in particular coagulation forceps, comprising two forcep arms which each have a free gripping end and which define a slit-like space, preferably tapering from the gripping ends in the rest position of the arms, and which can be resiliently moved towards each other and which extend from a common closed zone, and a gripping element.

Such forceps are pincer-like instruments with resilient arms for gripping and holding, such forceps being used predominantly in the surgical or dental-technical fields, in which respect anatomical forceps are grooved, surgical forceps are toothed and forceps for removing foreign bodies are provided with fine tips. A particular form thereof is constituted by what is known as coagulation forceps, the tips of which are supplied with current.

Forceps usually comprise resilient metal strips which bear against each other in the region of the part of the forceps referred to as the closed zone, and are there also welded or riveted together.

Having regard to that state of the art the inventor set himself the aim of providing tweezers or forceps of the kind set forth in the opening part of this specification, which are cheap and easy to produce and which provide a wide variety of uses. A particular aim on the part of the inventor is to provide disposable or one-trip forceps.

SUMMARY OF THE INVENTION

That object is attained in that the forceps comprise at least two shaped parts which subdivide the closed zone in the longitudinal direction and which are connected together with their inside surfaces bearing against each other, wherein in accordance with a further feature of the invention the forceps are divided on their longitudinal axis and each shaped or moulded part has a half of both forcep arms. The plane of separation therefore extends within the forcep arms and not in the slit-like space between the arms, as is known from the state of the art.

The shaped or moulded parts are of the same configuration, in a particularly advantageous embodiment, so that both production and storage are simplified. In addition it has been found desirable for the single forcep halves to be produced from plastic material and for the two forcep halves then to be joined together in such a way that longitudinal grooves which in accordance with the invention are disposed in the forcep arms and which extend through the entire body of the forceps are supplemented to define channels in the finished forceps.

The channels in accordance with the invention make it possible to fit separate gripping tips at the free ends of the forcep arms, to replace them or the like, and thus considerably to increase the variety of possible uses.

Another advantage of the forceps according to the invention is that for example in the case of coagulation forceps, the current lines which are connected to the gripping ends can be easily fitted into the channels which are produced by the longitudinal grooves; in a particularly advantageous embodiment the current conductors terminate at plug pins which in turn can each be fixed in a respective one of the channels. Preferably it is also possible to fit elongate members of electrically conductive material into those channels, forming at their ends on the one hand a gripping tip and on the other hand a contact pin.

It will be clear that the configuration of the forcep halves in accordance with the invention provides an extremely wide range of variations in forcep configurations, with a small storage requirement and simple assembly options.

An aspect of importance in regard to simplification of assembly is a pin which projects from the inside surface of the forceps half, with a blind hole of corresponding cross-section associated with the pin in mirror image relationship on the other side of the longitudinal axis of the forceps; when two forcep halves are fitted together the above-described components engage one into the other and thus permit rapid centering relative to each other and possibly even ensure that the two halves of the forceps are firmly held together.

A particular way of guiding the forcep arms in the gripping operation, that is to say when the forcep arms are moved towards each other, also lies within the scope of the invention. That configuration involves at least one pair of portions formed on the forcep arm halves, wherein advantageously such a portion extends from each of the forcep arms into the slit-like space, in such a way that the inside surface of one such portion slides along against the inside surface of the other such portion in the above-described gripping operation, thus providing for precise guidance when closing the gripping opening of the forceps. Another aspect of importance is that, by virtue of the forcep arms being of the same shape, the two pairs of portions formed on the sides of the forceps are in reverse mirror image relationship relative to each other. That considerably improves the guidance effect.

In the present case the gripping element which is engaged by the fingers of the surgeon or other user comprises radial ribs in the form of parts of rings, which form rings when the opening of the forceps is in a closed condition. Those part-ring ribs are formed by shaping peripheral grooves in the arms of the forceps structure. The rib surfaces are roughened by portions formed thereon.

The invention thus generally provides a simple throw-away article with the advantages already described hereinbefore.

BRIEF DESCRIPTION OF THE DRAWINGS

Further advantages, features and details of the invention will be apparent from the following description of preferred embodiments and with reference to the drawing in which:

FIG. 4 shows one of the forcep halves, FIG. 5 is a view on an enlarged scale in section taken along line V—V in FIG. 4.

FIGS. 6, 7 and 8 are end views as indicated by the arrows VI and VII respectively in FIG. 2 and arrow VIII in FIG. 4, and FIG. 9 is a sectional perspective view of part of the forceps.

DETAILED DESCRIPTION

Figure 1:
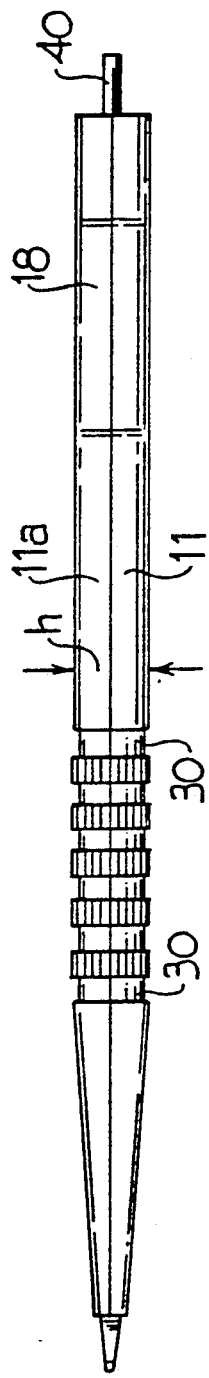
FIG. 1 is a plan view of a forcep instrument comprising two forcep halves.
Figure 2:
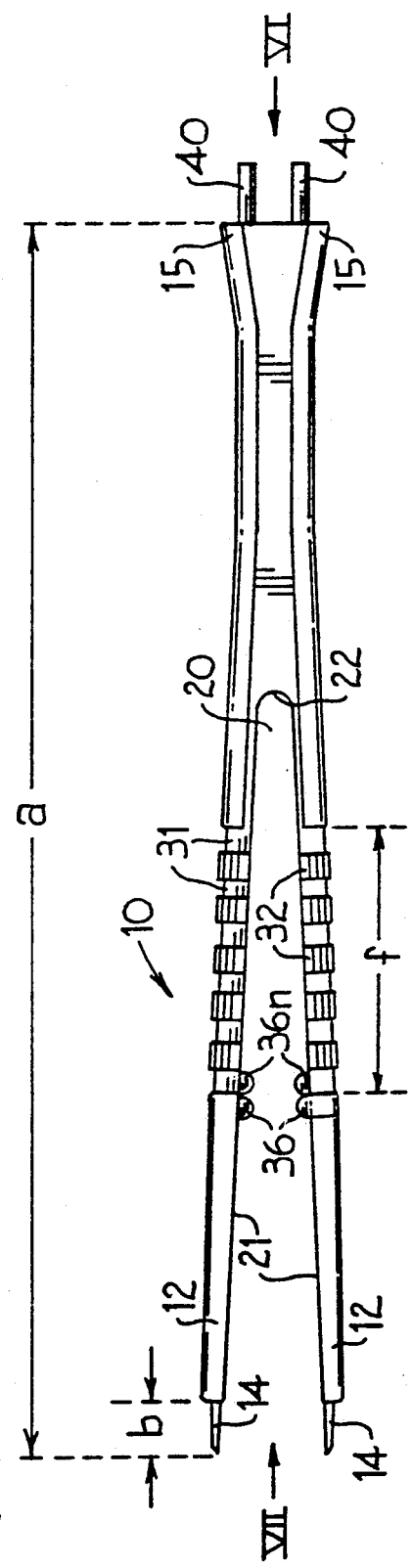
FIG. 2 is side view of the structure shown in FIG. 1 with the forceps in the rest condition.

A forceps or tweezer instrument 10 of a length for example of 150 mm, as indicated at a, as shown in particular in FIG. 1, comprises two forcep halves 11 and 11$_a$ which are of the same shape and which bear against each other with their inside surfaces 19. The forcep halves in this case together give a forcep height h of about 8 mm. Of the above-indicated overall length a of the forceps 10, the projection length b of two gripping tips 14 which are fitted into forcep arms 12 occupies a length of about 10 mm.

Referring to FIGS. 1 and 4, each forcep half 11 and 11$_a$ has a closed zone 18 which extends from an end face 16 which provides a fin-like enlargement portion 15. The length i of the closed zone 18 is about 60 mm while a slit-like space 20 which extends between the forcep arms 12 terminates at the closed zone 18. The space 20 begins at the ends 24 of the forcep arms 12 and the edges of the slot or forcep arms, as indicated at 21, converge in a tapering configuration at an acute angle w, to the deepest part as indicated at 22 of the slot-like shape. The taper angle w is greater than an angle t which is structurally delimited by the co-operation of two longitudinal grooves 26 flanking the slit 20. That means that in the region of the deepest part of the slit 22, the edges 21 of the forcep arms are disposed at a spacing q of for example 1.2 mm from the respectively adjacent longitudinal groove 26 as shown in FIG. 4. At the ends 24 the arms 12 extend almost exactly at the angle t of longitudinal grooves 26. The angle w formed between arms 12 is defined by inner groove walls 27 formed adjacent longitudinal groove 26, as shown in FIG. 5.

A gripping zone 30 of a length f of more than 30 mm begins approximately at a spacing e—in this case about 16 mm—from the deepest part 22 of the slit configuration; peripheral grooves 31 are provided to define ribs 32 which are in the form of part rings, with shaped portions thereof of triangular cross-section, providing a knurling configuration 33.

Figure 3:
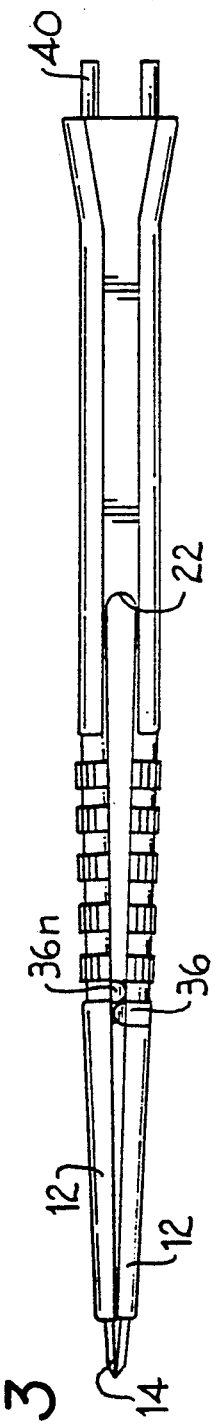
FIG. 3 is a view corresponding to that shown in FIG. 2 with the forceps in the gripping position.

Shown in FIG. 3 at the end of each gripping zone 30 which is towards the tip, on each forcep arm 12, is a knob-like shaped portion 36 and 36$_n$ which projects into the slot 20; the two portions 36 and 36$_n$ are laterally displaced relative to each other in the direction of the central line M of the forceps. The inside surface 37, which faces towards the center line M, of the portion 36, is in contact with the adjacent inside surface 37$_n$ of the other portion 36$_n$ in the gripping position shown in FIG. 3, that is to say when the forcep arms 12 are pressed towards each other. The contact between the pairs of portions 36/36$_n$ as described above provides for very precise guidance of the arms 12 of the forceps instrument during the gripping operation.

With reference to FIG. 4 projecting from the inside surface 19, outside of the center line M, is a pin 38 while a corresponding blind hole 39 is disposed opposite to the pin 38, in mirror image relationship therewith, on the other side of the center line M; when the two halves 11 and 11$_a$ of the forceps are fitted together the pin 38 of one half engages into the blind hole 39 in the other half. The longitudinal grooves 26 then also co-operate to define channels.

There is no need here to further describe the feature that tips 14 can be fixed in the channels defined in the forceps 12, by the longitudinal grooves 26, with the tips 14 being of any cross-sectional shape in regard to the free end. The point of significance is that the gripping tips 14 are supported non-rotatably in the longitudinal grooves 26, which can be done by virtue of a polygonal cross-section or by virtue of portions of an inwardly extending configuration or an outwardly extending configuration, in the longitudinal grooves, while portions of outwardly extending configuration and inwardly extending configuration respectively on the base portion of the tips then engage into the corresponding portions in the longitudinal grooves.

In the case of the illustrated forceps 10 which are used as coagulation forceps, the gripping tips 14 are connected to electrical cables which extend in the channels 26 and which terminate for example at plug pins 40 which in turn are fixed in the channels 26. In a particular embodiment each gripping tip 14 is part of a bar of electrically conductive material which is fitted into the channel 26 and which terminates in the form of a plug pin 40.

When the forceps 10 are used as one-way operation forceps, it will be apparent that the electrical fitments are omitted.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

I claim:

1. A forceps having upper and lower forceps arms joined at a proximal end by a common closed zone and open at a distal end thereby defining a slit-like space therebetween, said forceps comprising:
    a first longitudinal forceps element forming a portion of each of said upper and lower forceps arms and said common closed zone;
    a second longitudinal forceps element forming a mating portion of said upper and lower forceps arms and said common closed zone; and
    pin means for joining said first and second longitudinal forceps elements in a fixed position.

2. A forceps according to claim 1 wherein said first and second longitudinal forceps elements each define substantially one half of said forceps.

3. A forceps according to claim 1 further comprising separate gripping tips attached to said distal ends of said upper and lower forceps arms.

4. A forceps according to claim 1 further comprising alignment means formed in the upper and lower arm portions of said first and second longitudinal forceps elements.

5. A forceps according to claim 4 wherein said alignment means comprises at least one tab extending from each of said upper and lower forceps arms into said slit-like space therebetween such that as said arms are closed, said tabs serve to longitudinally align said upper and lower forceps arms.

6. A forceps according to claim 1 wherein the material of construction is moldable plastic.

7. A forceps according to claim 1 further comprising a gripping zone formed on each of said upper and lower forceps arms.

8. A forceps according to claim 7 wherein said gripping zone is formed of alternating peripheral grooves defining a plurality of annular ribs.

9. A forceps having grooved upper and lower forceps arms joined at a proximal end by a common closed zone and open at a distal end thereby defining a slit-like space therebetween, said forceps comprising:
   a first longitudinal forceps element forming a portion of each of said grooved upper and lower forceps arms and said common closed zone;
   a second longitudinal forceps element forming a mating portion of each of said grooved upper and lower forceps arms and said common closed zone; and
   pin means for joining said first and second longitudinal forceps elements in a fixed position.

10. A forceps according to claim 9 wherein said grooved upper and lower forceps arms define two separate axial channels extending from the proximate to the distal ends thereof.

11. A forceps according to claim 10 further comprising separate gripping means insertable into said channels in the distal ends of said upper and lower forceps arms.

12. A forceps according to claim 11 wherein said gripping means is formed of an electrically conducting material and said first and second longitudinal forceps sections are formed from an electrically insulating material.

13. A forceps according to claim 12 further comprising a plug pin electrically connected through said channels to each of said gripping means.

14. A forceps according to claim 9 further comprising a gripping zone formed on each of said upper and lower forceps arms.

15. A forceps according to claim 9 further comprising alignment means for accurately guiding said upper and lower forceps arms together as they are closed.

16. A forceps according to claim 9 wherein said pin means for joining said first and second longitudinal forceps elements comprises a pair of pins inserted into said common closed zone.

17. A process for fabricating a forceps having upper and lower forceps arms joined at a proximal end of a common closed zone and open at a distal end thereby defining a slit-like space therebetween, said process comprising the steps of:
   providing a first integrally formed longitudinal forceps element including a portion of each of said upper and lower forceps arms and a portion of said common closed zone;
   providing a second integrally formed longitudinal forceps element including a mating portion of said upper and lower forcep arms and a mating portion of said common closed zone; and
   fixedly joining said first and second longitudinal forceps elements.

18. A process according to claim 17 wherein said steps of joining said first and second longitudinal forceps elements is accomplished by inserting at least one pin into said portions of said common closed zone.

19. A process according to claim 17 further comprising the steps of forming an axial channel in each of said upper and lower forceps arms and inserting electrically conducting gripping means in each of said axial channels.

20. A forceps formed in accordance with the process of claim 17.

* * * * *